(12) United States Patent
Gopinathan et al.

(10) Patent No.: US 6,757,556 B2
(45) Date of Patent: Jun. 29, 2004

(54) ELECTRODE SENSOR

(75) Inventors: Govindan Gopinathan, Oradell, NJ (US); Arthur R. Tilford, Yorba Linda, CA (US)

(73) Assignee: Ineedmd. com, Great Neck, NY (US)

(*) Notice: Subject to any disclaimer, the term of this patent is extended or adjusted under 35 U.S.C. 154(b) by 0 days.

(21) Appl. No.: 09/971,204

(22) Filed: Oct. 4, 2001

(65) Prior Publication Data

US 2002/0016538 A1 Feb. 7, 2002

Related U.S. Application Data

(63) Continuation-in-part of application No. 09/884,371, filed on Jun. 19, 2001, now Pat. No. 6,595,918, and a continuation-in-part of application No. 09/741,283, filed on Dec. 19, 2000, now Pat. No. 6,540,673, said application No. 09/884,371, is a continuation of application No. 09/188,971, filed on Nov. 10, 1998, now Pat. No. 6,248,064, which is a continuation-in-part of application No. 09/084,647, filed on May 26, 1998, now Pat. No. 6,224,548, said application No. 09/741,283, is a continuation of application No. 09/084,647.

(51) Int. Cl.[7] .............................................. A61B 5/04
(52) U.S. Cl. ...................... 600/372; 600/382; 600/383; 600/397; 607/149; 607/150; 607/153
(58) Field of Search ................................ 600/372, 382, 600/383, 397; 607/139, 140, 149, 150, 153

(56) References Cited

U.S. PATENT DOCUMENTS

| | | | |
|---|---|---|---|
| 206,474 A | 7/1878 | Morel | |
| 2,621,657 A | * 12/1952 | Leech | 600/397 |
| 3,508,541 A | * 4/1970 | Westbrook et al. | 600/383 |
| 3,659,614 A | * 5/1972 | Jankelson | 607/139 |
| 3,845,771 A | * 11/1974 | Vise | 607/150 |
| 3,888,240 A | 6/1975 | Reinhold, Jr. et al. | |
| 4,014,323 A | * 3/1977 | Gilmer et al. | 600/372 |
| 4,016,868 A | 4/1977 | Allison | |
| 4,033,334 A | * 7/1977 | Fletcher et al. | 600/383 |
| 4,062,364 A | * 12/1977 | Masaki | 607/153 |
| 4,230,127 A | 10/1980 | Larson | |
| 4,381,012 A | 4/1983 | Russek | |
| 4,510,939 A | 4/1985 | Brenman et al. | |
| 4,583,547 A | 4/1986 | Granek et al. | |
| 4,608,987 A | 9/1986 | Mills | |
| 4,662,378 A | 5/1987 | Thomis | |
| 4,698,848 A | 10/1987 | Buckley | |
| 4,706,679 A | * 11/1987 | Schmidt et al. | 600/383 |
| 4,709,704 A | 12/1987 | Lukasiewicz | |
| 4,765,343 A | * 8/1988 | Brenman et al. | 600/384 |
| 4,974,607 A | 12/1990 | Miwa | |
| 5,007,427 A | 4/1991 | Suzuki et al. | |
| 5,224,479 A | 7/1993 | Sekine | |
| 5,345,934 A | * 9/1994 | Highe et al. | 600/372 |
| 5,353,793 A | 10/1994 | Bornn | |
| 5,431,170 A | 7/1995 | Mathews | |
| 5,442,729 A | 8/1995 | Kramer et al. | |
| 5,465,727 A | 11/1995 | Reinhold, Jr. | |
| 5,511,546 A | 4/1996 | Hon | |
| 5,626,151 A | 5/1997 | Linden | |
| 5,640,953 A | 6/1997 | Bishop et al. | |
| 5,666,404 A | 9/1997 | Ciccotelli et al. | |
| 5,670,944 A | 9/1997 | Myllymaki | |
| 5,687,738 A | 11/1997 | Shapiro et al. | |

(List continued on next page.)

FOREIGN PATENT DOCUMENTS

EP 0 459 239 A2 12/1991

*Primary Examiner*—Lee Cohen
(74) *Attorney, Agent, or Firm*—Brooks Kushman P.C.

(57) ABSTRACT

The present invention involves an electrode sensor attachable to a substrate for sensing electrical activity of a patient. The electrode sensor comprises an elongated conductive body having first and second ends, wherein the first end is adapted to contact the patient for sensing electrical activity of the patient. The second end is configured to conductively attach to the substrate. The elongated conductive body is greater than about 2 millimeters in length and is configured to extend from the substrate.

53 Claims, 4 Drawing Sheets

U.S. PATENT DOCUMENTS

| | | |
|---|---|---|
| 5,704,364 A | 1/1998 | Saltzstein et al. |
| 5,730,140 A | 3/1998 | Fitch |
| 5,738,104 A | 4/1998 | Lo et al. |
| 5,771,001 A | 6/1998 | Cobb |
| 5,771,891 A | 6/1998 | Gozani |
| 5,855,550 A | 1/1999 | Lai et al. |
| 5,877,675 A | 3/1999 | Rebstock |
| 6,022,321 A | 2/2000 | Amano et al. |
| 6,217,523 B1 | 4/2001 | Amano et al. |
| 6,224,548 B1 | 5/2001 | Gopinathan et al. |
| 6,248,064 B1 | 6/2001 | Gopinathan et al. |

* cited by examiner

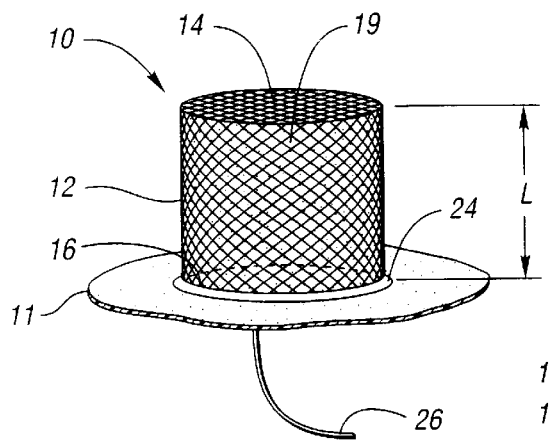
*Fig. 1*
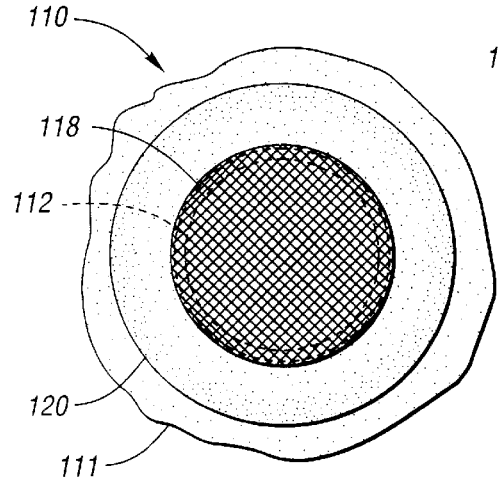
*Fig. 2b*
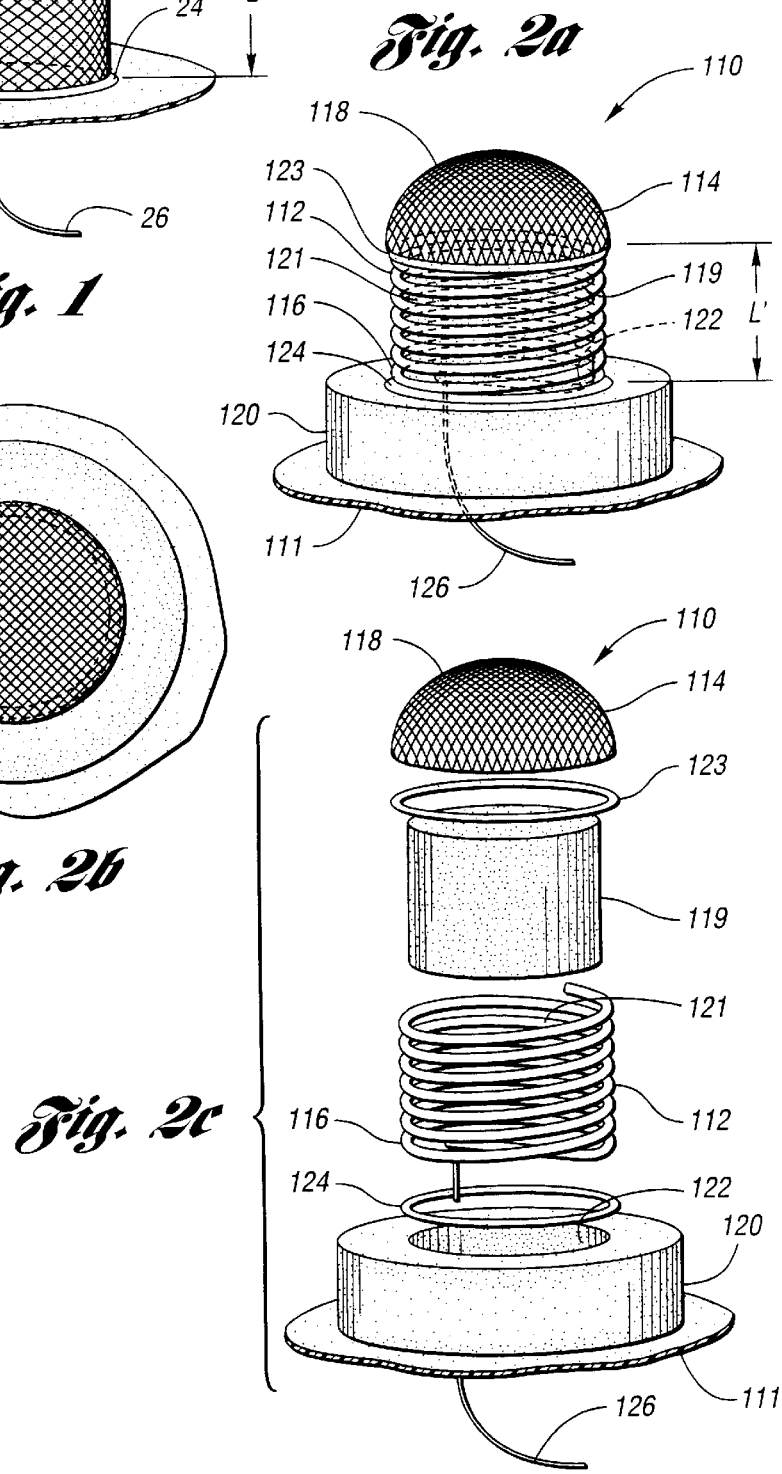
*Fig. 2a*
*Fig. 2c*

ELECTRODE SENSOR

CROSS-REFERENCE TO RELATED APPLICATIONS

This application is a continuation-in-part of U.S. patent application Ser. Nos. 09/884,371, filed Jun. 19, 2001, now U.S. Pat. No. 6,595,918, and 09/741,283, filed Dec. 19, 2000 now U.S. Pat. No. 6,540,673. U.S. patent application Ser. No. 09/884,371 is a continuation of U.S. patent application Ser. No. 09/188,971, filed Nov. 10, 1998, now U.S. Pat. No. 6,248,064, issued on Jun. 19, 2001, which is a continuation-in-part of U.S. patent application Ser. No. 09/084,647, filed May 26, 1998, now U.S. Pat. No. 6,224,548, issued on May 1, 2001. U.S. patent application Ser. No. 09/741,283 is a continuation of U.S. patent application Ser. No. 09/084,647, filed May 26, 1998, now U.S. Pat. No. 6,224,548, issued May 1, 2001.

BACKGROUND OF THE INVENTION

1. Field of the Invention

The present invention relates to electrode sensors and assemblies thereof attachable to a substrate for sensing electrical activity of a patient. The present invention also relates to methods of making and using such electrode sensors and assemblies.

2. Background Art

Diagnostic devices which gather and transmit diagnostic information are known and have been used for years. These devices may gather and transmit information such as Electrocardiogram (EKG), Blood Pressure (BP), pulse, and body temperature. Such devices are known to gather electrical activity of a patient to diagnose a patient's condition, e.g., heart activity. Although many of these devices are sufficient in gathering such information, many of these devices are limited in the quality and types of diagnostic information they can gather and transmit.

Although many sensors for EKG diagnostic devices adequately sense electrical activity of a patient, the quality of the sensors can be improved. For example, many of these sensors are flat, solid members. The structural design of these sensors results in limitations as to the manner in which the sensors gather information. More particularly, the design of these sensors essentially calls for the sensors to be separately positioned on a patient in order to gather and transmit information. However, challenges occur when these sensors are attached onto a unitary structure. In such circumstances, sufficient contact with the patient is not consistently obtained, resulting in unacceptable readings, e.g., EKG readings. In many situations, this is due to discontinuities and unevenness regarding the contour of a patient's body. Attaching the sensors onto a unitary structure reduces the average surface area contact between each sensor and the patient's body. Moreover, these sensors do not enhance surface area contact with the patient's body because these sensors typically have an unsubstantial height and are non-permeable. Additionally, hair on the patient's body also interfere with obtaining an adequate reading.

SUMMARY OF THE INVENTION

Thus, it is an object of the present invention to provide sensors for a diagnostic device which gathers and transmits diagnostic information, wherein the sensors may be attached onto a unitary structure during use of the device while maintaining sufficient contact with the patient to provide acceptable readings.

It is another object of the present invention to provide an improved electrode sensor having an improved contact area with an increased surface area.

It is yet another object of the present invention to provide an improved electrode sensor having a length greater than about 2 millimeters.

It is another object of the present invention to provide an electrode sensor attachable to a substrate for sensing electrical activity of a patient.

The above and other objects of the present invention are achieved providing an electrode sensor that comprises an elongated conductive body having first and second ends, wherein the first end is contactable with the patient for sensing electrical activity of the patient. The second end is attachable to the substrate. The elongated conductive body extends from the substrate and is greater than about 2 millimeters in length.

Another embodiment of the present invention provides an electrode sensor attachable to a substrate for sensing electrical activity of a patient and allowing a non-conductive or conductive fluid to be permeated therethrough. The electrode sensor comprises a conductive body having first and second ends. The first end is permeable to allow the fluid to be absorbed therethrough and adapted to receive the fluid thereon to contact the patient for sensing electrical activity of the patient. The second end is configured to be conductively attachable.

In yet another embodiment of the present invention, an electrode sensor assembly comprises an elongated conductive body having first and second ends, wherein the first end is adapted to contact a patient for sensing electrical activity of the patient. The second end is configured to be conductively attachable, wherein the elongated conductive body is greater than about 2 millimeters in length. The assembly further comprises a substrate to which the second end is attached, allowing the elongated conductive body to extend from the substrate to contact the patient.

In another embodiment of the electrode sensor assembly, the assembly comprises a conductive body having first and second ends, wherein the first end is adapted to receive the fluid thereon and to contact the patient for sensing electrical activity of the patient. The second end is configured to be conductively attachable, wherein the conductive body is permeable to allow the fluid to pass therethrough. The assembly further comprises a substrate to which the second end is attached. This allows the elongated conductive body to extend from the substrate to contact the patient.

It is another object of the present invention to provide an electrode sensor for sensing electrical activity of a patient and sending signals to a processor. The sensor further comprises an elongated tubular body being greater than two millimeters and being permeable to allow fluid to be absorbed therethrough. The elongated body has first and second ends and it is made of conductive material. The first end is connected to the head so that the elongated body is in conductive communication with the head. The connection of the elongated tubular body to the conductive head defines an inner space within the body and the head. Moreover, the elongated body has a conductive wire connected to the second end. The electrode sensor further comprises an absorbent material disposed in the inner space for absorbing fluid applied on the head, and a ceramic base having an aperture in which the second end of the elongated body is disposed. The conductive wire is disposed through the aperture and adapted to be conductively connected to the processor.

It is yet another object of the present invention to provide a method of making an electrode sensor which is attachable to a substrate and usable for sensing electrical activity of a patient. The method comprises providing a conductive head to contact the patient for sensing electrical activity, wherein the conductive head is permeable to allow fluid to pass therethrough. The method further comprises providing an elongated tubular body being greater than two millimeters in length and being made of conductive material. The elongated tubular body has first and second ends, wherein the elongated body has a conductive wire connected to the second end. The method further includes providing an absorbent material and a ceramic base having an aperture. The method further comprises connecting the first end of the elongated tubular body to the conductive head so that the elongated body is in conductive communication with the head. The connection of the elongated tubular body to the conductive head defines an inner space within the body and the head. The method further comprises disposing the absorbent material in the inner space for absorbing fluid applied on the head, and disposing the second end of the elongated body in the aperture, wherein the conductive wire is disposed through the aperture and adapted to be conductively attachable.

It is still yet another object of the present invention to provide a method of sensing electrical activity of a patient with an electrode sensor. The method comprises providing a conductive head to contact the patient for sensing electrical activity, wherein the conductive head is permeable to allow conductive fluid to pass therethrough. The method further comprises providing an elongated tubular body which is greater than two millimeters in length and is permeable to allow fluid to pass therethrough. The elongated body has first and second ends and is made of conductive material. The first end is connected to the head so that the elongated body is in conductive communication with the head. The connection of the elongated tubular body to the conductive head defines an inner space within the body and the head. The elongated body has a conductive wire connected to the second end. The method further comprises providing an absorbent material disposed in the inner space for absorbing fluid applied on the head, and providing a ceramic base having an aperture in which the second end of the elongated body is disposed. The conductive wire is disposed through the aperture and adapted to be conductively connected to a processor. The method further includes applying conductive fluid onto the conductive head, contacting the conductive head to the patient, and maintaining contact of the conductive head to the patient to sense electrical activity of the patient.

In yet another embodiment of the electrode sensor, the electrode sensor is attachable to a substrate for sensing electrical activity of a patient. The electrode sensor includes an elongated conductive body that is greater than about 2 millimeters in length and is configured to extend from the substrate.

In still yet another embodiment of the electrode sensor, the electrode sensor includes a conductive body having first and second ends, wherein the first end is permeable to contact a patient for increased surface area in sensing electrical activity of the patient. The second end is configured to be conductively attachable.

BRIEF DESCRIPTION OF THE DRAWINGS

FIG. 1 is a side view of an electrode sensor in accordance with the present invention;

FIG. 2a is a side view of another embodiment of the sensor of FIG. 1;

FIG. 2b is a top view of the sensor in FIG. 2a;

FIG. 2c is an exploded view the sensor in FIG. 2a;

DETAILED DESCRIPTION OF THE PREFERRED EMBODIMENTS

Figure 3:
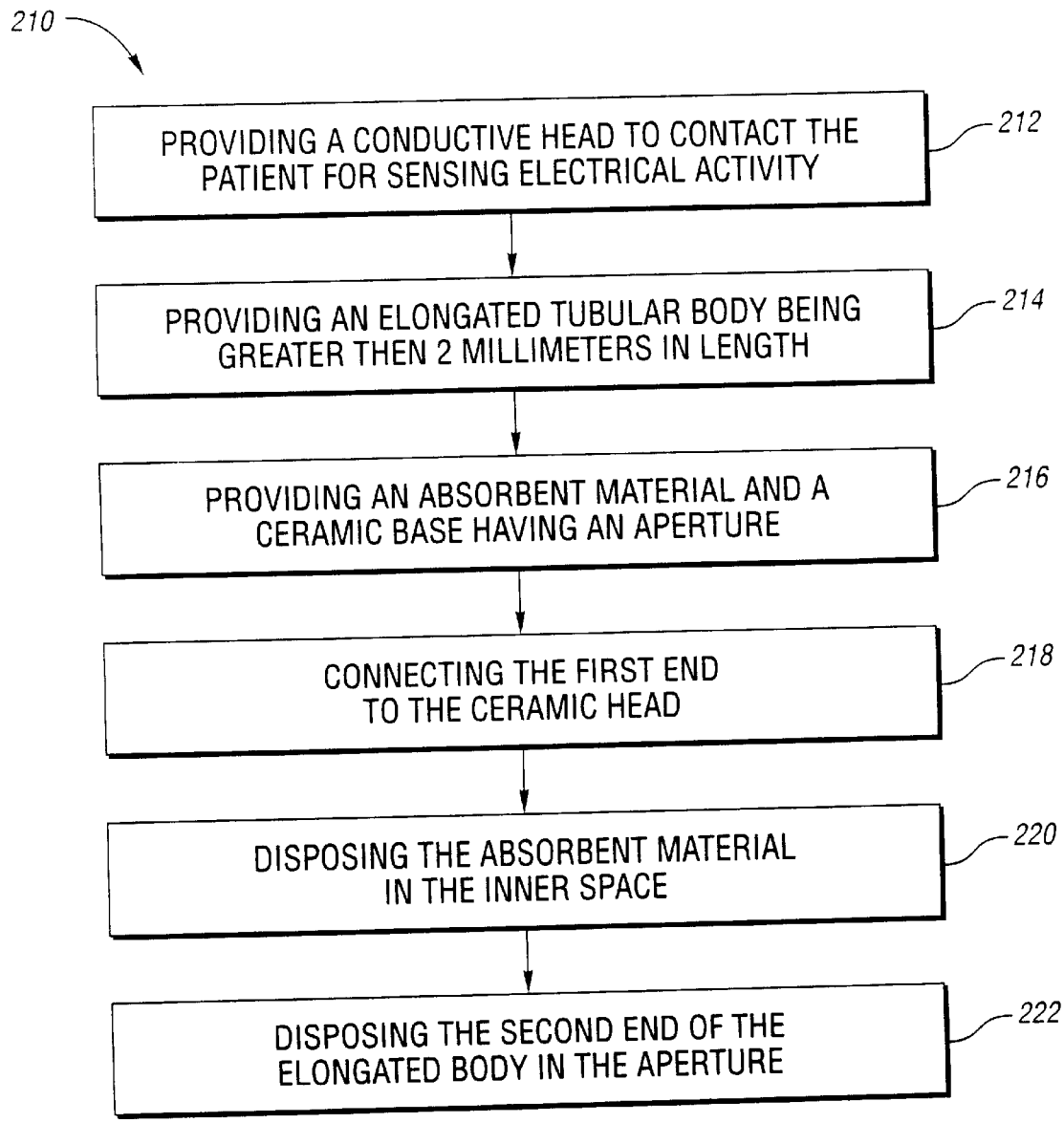
FIG. 3 is a flow chart depicting a method of making the electrode sensor of FIG. 1.

FIG. 1 generally illustrates one embodiment of an electrode sensor in accordance with the present invention and depicted as reference numeral 10. Electrode sensor 10 is attachable to substrate 11 for sensing electrical activity of a patient (not shown). A patient may be defined as a living body from which electrical activity may be sensed. This preferably but not necessarily includes humans, mammals, and animals. As shown, electrode sensor 10 comprises an elongated conductive body 12 having first and second ends 14 and 16. Body 12 may take on a tubular shape, but may be rectangular, trapezoidal, or any other suitable shape. Such suitable shapes used would not fall beyond the scope or spirt of the present invention. Preferably, but not necessarily, body 12 is permeable to allow non-conductive or conductive fluid to be permeated and absorbed therethrough. Body 12 has length L which is greater than about two millimeters (mm) and preferably is about 8.0 mm, more preferably about 10.0 mm, and most preferably about 12.0 mm. In this embodiment, elongated conductive body 12 is made of conductive material to facilitate sensing electrical activity of the patient. For example, body 12 may be made of a conductive mesh or a conductive spring. Of course, other suitable structures which allow for permeability therethrough do not fall beyond the scope or spirit of the present invention.

It is to be noted that the body may be made of any suitable conductive material. For example, copper may be used or ceramic material with silver oxide may be used.

First end 14 is permeable to allow fluid, such as conductive fluid, to be absorbed therethrough and is adapted to receive the fluid thereon to contact the patient for sensing electrical activity of the patient. Conductive fluid, as known in the art, facilitates conductivity between a patient and sensor 10. For example, conductive fluid which may be use include but is not limited to potassium chloride or sodium chloride. As shown, first end 14 is planar, but may be essentially planar or arcuate without falling beyond the scope or spirit of the present invention. First end 14 may be comprised of a conductive mesh material. The conductive mesh material have a size of preferably about 0.8 mm, more preferably about 1.2 mm, and most preferably about 1.0 mm mesh welded at cross points for conductivity.

The first end 14 may be pressed against the contour a patient's body to define a contact area of sensor 10. The mesh configuration of first end 14 allows an increased surface area contact with the patient relative to a non-mesh configuration. In turn, more accurate results in sensing electrical activity of the patient can be gathered. Second end 16 is configured to attach to substrate 11. This may be accomplished by using epoxy resin 24 or other suitable adhesives as known in the art to bond second end 16 to substrate 11. Substrate 11 may be any suitable non-conductive material to which second end 16 may attach. For example, substrate 11 may be a glove probe described in U.S. Pat. Nos. 6,224,548 and 6,248,064 and U.S. Published Application 2001-0056227 which are hereby incorporated by reference. As shown in FIG. 1, body 12 further includes conductive wire 26 which is connected by any suitable means to body 12 adjacent second end 16 and extends to substrate 11.

Elongated conductive body 12 may be a conductive spring having a predetermined tension so that the spring compresses when pressed against a patient. This facilitates further enhanced surface area contact between first end 14 and the patient during use of electrode sensor 10. Although in this embodiment sensor 10 includes elongated body 12 which is a conductive spring, elongated body 12 may be any other suitable form which facilitates "breathing" or fluid flow therethrough. For example, body 12 may be made of a conductive mesh material.

As shown in FIG. 1, elongated body 12 is preferably hollow defining an inner space 21 within body 12. Inner space 21 complements the shape of body 12. As shown, absorbent material 19 is disposed within inner space 21 for absorbing fluid applied on first end 14. In this embodiment, absorbent material 19 is a sponge material, but may be any other suitable absorbent material without falling beyond the scope or spirit of the present invention. Thus, as elongated conductive body 12 is a conductive spring, a predetermined tension of the spring allows sensor 10 to be compressed when pressure is placed on first end 14 having absorbent material 19 applied thereon. This facilitates absorption of conductive fluid by absorbent material 19 when fluid is disposed on first end 14 and when the first end 14 is in contact with the patient.

FIG. 2a illustrates another embodiment of an electrode sensor attachable to a substrate for sensing electrical activity of a patient. In FIG. 2a, electrode sensor 110 is attachable to substrate 111, wherein sensor 110 comprises an elongated conductive body 112 similar to the embodiment described above. Body 112 has first and second ends 114 and 116. As in the embodiment described above, elongated conductive body 112 has length L' which is greater than about two millimeters in length. Body 112 is permeable to allow fluid to be absorbed therethrough, wherein first end 114 of body 112 is adapted to receive and absorb fluid thereon. Body 112 may include conductive mesh for such permeability and absorption therethrough. Preferably, but not necessarily, body 112 is made of a conductive metallic spring having a predetermined tension. The predetermined tension allows the spring to compress when pressure is applied onto the patient to facilitate close contact with the patient's skin and absorption of conductive fluid. Elongated conductive body 112 may be tubular in shape, but may take on any other suitable shape without falling beyond the scope or spirit of the present invention. Second end 116 is configured to conductively attach to base 120 preferably but not necessarily made of ceramic. Second end 116 also includes conductive wire 126 which is connected thereto and extends to base 120 to facilitate in conductively connecting sensor 110 to substrate 111.

As shown in FIGS. 2a–b, sensor 110 further includes a conductive head 118 which is connected to first end 114 of body 112 so that head 118 is in conductive communication with body 112. Head 118 may be connected to first end 114 with a conductive epoxy resin 123. As known in the art, conductive epoxy resin may include Circuit Works™ CW2400 parts A and B from Chemtronics, Inc., or H₂OE™ parts A and B from Epoxy Technology, Inc. Head 118 is adapted to contact a patient for sensing electrical activity of the patient. The connection of conductive head 118 to elongated body 112 defines an inner space 121 within head 118 and body 112. Inner space 121 complements the shapes of head 118 and body 112. Head 118 may be attached to body 112 with use of epoxy resin 124 as known in the art. Conductive head 118 is configured to contact the patient for sensing electrical activity, and is permeable to allow conductive fluid to be absorbed therethrough. Thus, conductive head 118 may be made of conductive mesh to facilitate permeation and provide an increased surface area contact when pressure is applied onto the patient. As shown in FIGS. 2a–c, conductive head 118 is arcuately shaped and is connected to first end 114 of elongated conductive body 112 to define an arcuate surface of conductive head 118. Of course, head 118 may take on others shapes such as slanted, essentially planar, pointed, or any other suitable shapes. The arcuate surface is configured to nestle upon contour surfaces of the patient.

As shown in FIGS. 2a–c, absorbent material 119 is disposed within inner space 121 for absorbing fluid applied on the head. Conductive fluid, as known in the art, facilitates conductivity between the patient and the sensor. Absorbent material 119 may be in contact with conductive head 118 and body 112. In this embodiment, elongated conductive body 112 is a conductive spring, wherein a predetermined tension of the spring allows sensor 110 to be corn pressed when pressure is applied on the head 118. This facilitates absorption of conductive fluid by the absorbent material 119 when fluid is disposed on the head 118 and the head 118 is in contact with the patient. In this embodiment, absorbent material 119 may be a sponge material.

As shown in FIGS. 2a–c, sensor 110 further includes base 120 having aperture or opening 122 in which second end 116 of body 112 is disposed. As shown, base 120 is attached by any suitable means, e.g., epoxy resin, to substrate 111 which is similar to substrate 11 in the embodiment described above. Conductive wire 126 is disposed through aperture 122 and is adapted to extend to substrate 111 and to be conductively attachable. In this embodiment, base 120 is made of ceramic material which is non-conductive. As ceramic base 120 is connected to substrate 111, wire 126 is fed through aperture 122 to substrate 111.

FIG. 3 illustrates a general method 210 of making an electrode sensor depicted in FIGS. 2a–c which is attachable to a substrate and is used for sensing electrical activity of a patient. As shown, method 210 comprises providing a conductive head to contact the patient for sensing electrical activity in block 212 wherein the conductive head is permeable to allow fluid to pass therethrough. The conductive head may initially be a planar mesh material which is formed to have an arcuate shape. It has been found that in many situations an arcuately shaped head enhances conductive contact with the patient and provides a nestled fit. Method 210 further includes providing an elongated tubular body which is greater than two millimeters in length and has first and second ends in block 214. The elongated tubular body is made of conductive material and has a conductive wire connected to the second end. The tubular body is configured to allow "breathing" or fluid flow therethrough as in air and/or conductive fluid. Preferably but not necessarily the body may be a conductive spring having a predetermined tension. Method 210 further includes providing an absorbent material and a non-conductive base having an aperture as shown in block 216. The absorbent material, as described above, may be any suitable absorbent material such as a sponge. The base may be any suitable non-conductive material such as ceramic. Method 210 further includes connecting the first end of the elongated tubular body to the conductive head so that the elongated tubular body is in conductive communication with the head as shown in block 218. A conductive epoxy resin 123 may be used to connect the body to the head. The connection of the elongated tubular body to the conductive head defines an inner space within the body and the head. The inner space complements the shapes of the head and the body. Next, method 210 includes disposing the absorbent material in the inner space for absorbing the conductive fluid applied on the head in block 220. The method 210 further includes disposing the second end of the elongated body in the aperture of the base in block 222, wherein the conductive wire is disposed through the aperture and adapted to be conductively attachable.

Figure 4:
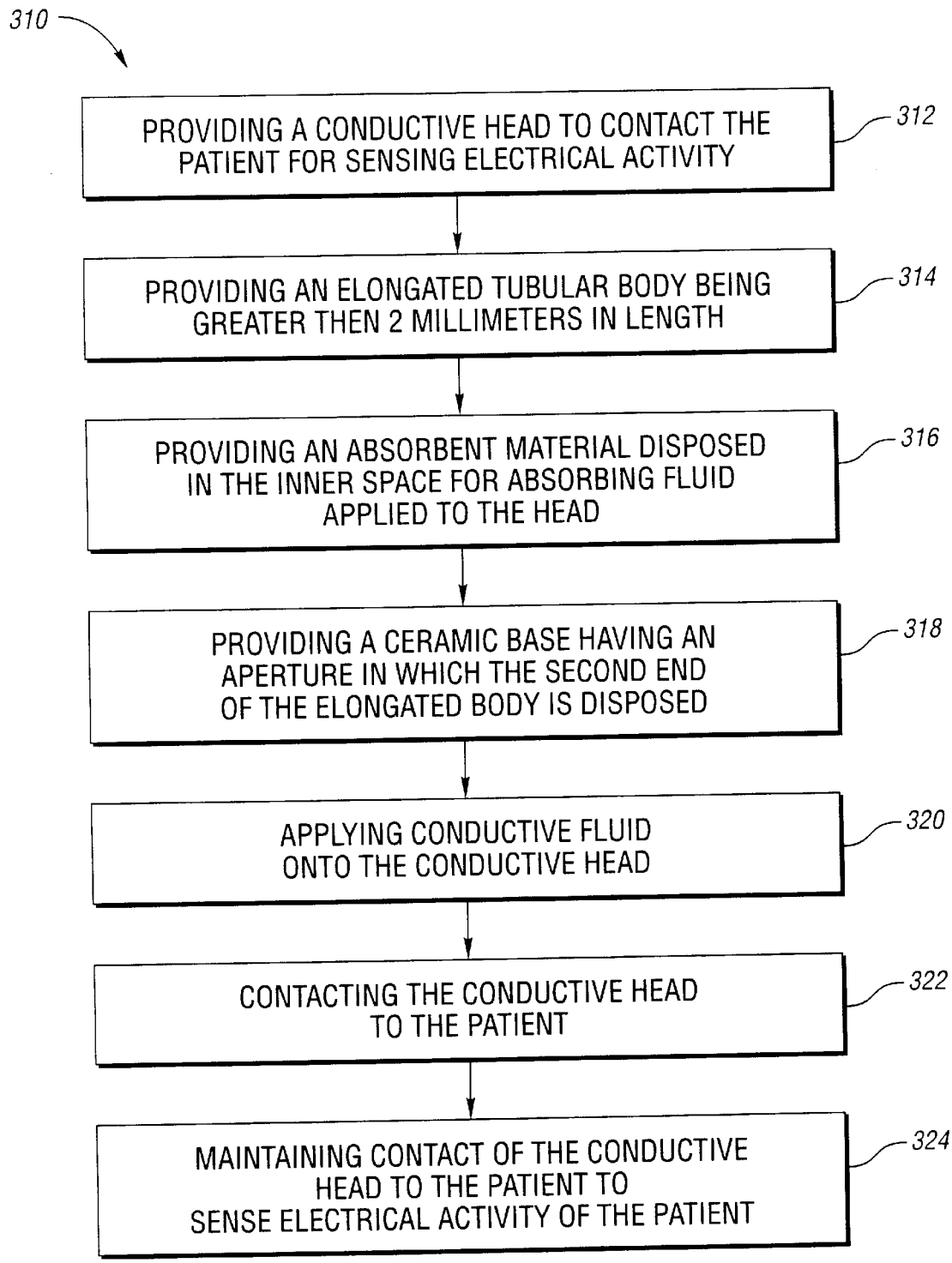
FIG. 4 is another flow chart depicting a method of sensing electrical activity with the sensor of FIG. 1.

FIG. 4 provides a method 310 of sensing electrical activity of a patient with the electrode sensor attached to a substrate as described above. Method 310 includes providing a conductive head, as described above, to contact the patient for sensing electrical activity in block 312, wherein the conductive head is permeable to allow conductive fluid to pass therethrough. Method 310 further includes providing an elongated tubular body which is greater than two millimeters in length and is permeable to allow fluid to pass therethrough in block 314. As described above, the elongated body has first and second ends and is made of conductive material, wherein the first end is connected to the head so that the elongated body is in conductive communication with the head. The connection of the elongated tubular body to the conductive head defines an inner space within the body and the head. The elongated body has a conductive wire connected to the second end.

Figure 5:
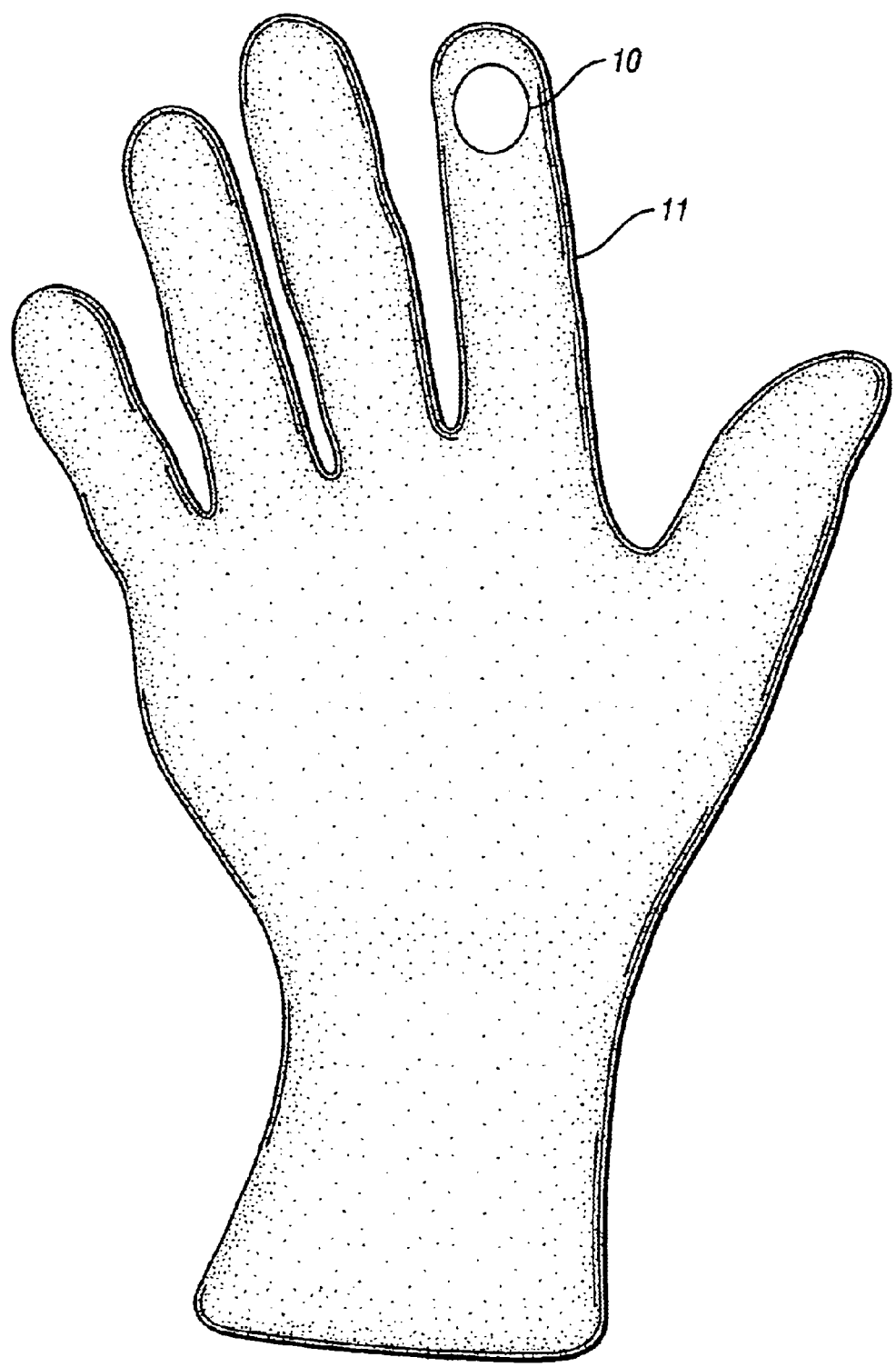
FIG. 5 is a schematic plan view of a glove probe illustrating an electrode sensor in accordance with the present invention.

FIG. 5 illustrates a glove probe 11 having an electrode sensor 10 in accordance with the present invention attached thereto. As shown in FIG. 5, the electrode sensor 10 is represented schematically. Moreover, it should be understood that one or more electrode sensors 10 can be placed throughout the glove probe 11 at various locations. For example, the glove probe 11 could have electrode sensors placed throughout as shown in the glove probes illustrated in U.S. Pat. Nos. 6,224,548, 6,248,064 and U.S. Published Application No. US 2001/0,056,227.

Method 310 further includes providing an absorbent material, as described above, disposed in the inner space for absorbing fluid applied on the head as shown in box 316, and providing a ceramic base having an aperture in which the second end of the elongated body is disposed as shown in block 318. The base may be attached to the substrate. The conductive wire is disposed through the aperture and adapted to be conductively connectable in the substrate. Method 310 further includes applying conductive fluid onto the conductive head in block 320 and contacting the patient with the conductive head in block 322. Method 310 further includes maintaining contact of the conductive head to the patient to sense electrical activity of the patient in block 324.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An electrode sensor attachable to a substrate for sensing electrical activity of a patient, the electrode sensor comprising:

an elongated conductive resilient body having first and second ends and a conductive wire, the first end contactable with the patient for sensing electrical activity of the patient, the second end being configured to attach to the substrate;

a conductive head connected to the first end of the elongated conductive body so that the head is in conductive communication with the elongated body, the connection of the conductive head to the elongated body defining an inner space within the head and the body, the inner space complementing the shapes of the head and the body, the conductive head being configured to contact the patient for sensing electrical activity and being permeable to allow conductive fluid to be absorbed therethrough; and an absorbent material disposed in the inner space for absorbing fluid applied on the head, the absorbent material being in contact with the conductive head and the elongated body.

2. The electrode sensor of claim 1 wherein a portion of the elongated body is permeable to allow fluid to be absorbed therethrough, the first end of the elongated conductive body is adapted to receive and absorb fluid thereon.

3. The electrode sensor of claim 2 wherein the elongated body includes a portion made of conductive mesh.

4. The electrode sensor of claim 1 wherein the first end is arcuate.

5. The electrode sensor of claim 1 wherein the elongated conductive body is tubular and the conductive wire is connected to the second end.

6. The electrode sensor of claim 5 wherein the conductive body is made of metal.

7. The electrode sensor of claim 1 wherein the conductive head is connected to the first end of the elongated conductive body with conductive epoxy resin.

8. The electrode sensor of claim 1 wherein the elongated conductive body is a metallic spring, the spring having a predetermined tension so that the spring compresses when pressure is applied on the head, facilitating absorption of conductive fluid by the absorbent material when fluid is disposed on the head and the head is in contact with the patient.

9. The electrode sensor of claim 1 wherein the absorbent material is a sponge material.

10. The electrode of claim 1 wherein the conductive head is made of conductive mesh.

11. The electrode of claim 1 wherein the conductive head is arcuately connected to the first end of the elongated conductive body to define a arcuate surface of the conductive head, the arcuate surface configured to nestle upon contour surfaces of the patient.

12. The electrode sensor of claim 1 wherein the elongated conductive body is a metallic spring.

13. The electrode sensor of claim 1 wherein the conductive body is made of conductive mesh.

14. The electrode sensor of claim 1 wherein the substrate is a wearable substrate.

15. The electrode sensor of claim 1 wherein the substrate is a glove.

16. The electrode sensor of claim 1 wherein the elongated conductive body is adapted to extend from the substrate and is greater than about 2 millimeters in length.

17. The electrode sensor of claim 1 further comprising a base having an aperture in which the second end of the elongated body is disposed, the conductive wire being disposed through the aperture and adapted to be conductively adapted to pass to the substrate.

18. An electrode sensor attachable to a glove probe for sensing electrical activity of a patient and allowing a fluid to be permeated therethrough, the electrode sensor comprising:
   a conductive body having first and second ends and a conductive wire, the first end being permeable to allow the fluid to be absorbed therethrough and adapted to receive the fluid thereon to contact the patient for sensing electrical activity of the patient, the second end being configured to be conductively attachable;
   a conductive head connected to the first end of the conductive body so that the head is in conductive communication with the body, the connection of the conductive head to the body defining an inner space within the head and the body, the inner space complementing the shapes of the head and the body, the conductive head being configured to contact the patient for sensing electrical activity and being permeable to allow conductive fluid to be absorbed therethrough; and
   an absorbent material disposed in the inner space for absorbing fluid applied on the head, the absorbent material being in contact with the conductive head and the body.

19. The electrode sensor of claim 18 wherein the conductive body is made of conductive mesh.

20. The electrode sensor of claim 18 wherein the conductive body is tubular and the conductive wire is connected to the second end.

21. The electrode sensor of claim 18 wherein the conductive head is connected to the first end of the conductive body with conductive epoxy resin.

22. The electrode sensor of claim 18 wherein the conductive body is a metallic spring, the spring having a predetermined tension so that the spring compresses when pressure is applied on the head, facilitating absorption of conductive fluid by the absorbent material when fluid is disposed on the head and the head is in contact with the patient.

23. The electrode sensor of claim 18 wherein the absorbent material is a sponge material.

24. The electrode sensor of claim 18 wherein the conductive head is made of conductive mesh.

25. The electrode sensor of claim 18 wherein the conductive head is arcuately connected to the first end of the conductive body to define a arcuate surface of the conductive head, the arcuate surface configured to nestle upon contour surfaces of the patient.

26. The electrode sensor of claim 18 further comprising a base having an aperture in which the second end of the body is disposed, the conductive wire being disposed through the aperture and adapted to pass through the glove probe.

27. An electrode sensor assembly for sensing electrical activity of a patient, the electrode sensor assembly comprising:
   an elongated conductive body having first and second ends and a conductive wire, the first end being adapted to contact the patient for sensing electrical activity of the patient;
   a substrate to which the second end is attached, allowing the elongated conductive body to extend from the substrate to contact the patient;
   a conductive head connected to the first end of the elongated conductive body so that the head is in conductive communication with the elongated body, the connection of the conductive head to the elongated body defining an inner space within the head and the body, the inner space complementing the shapes of the head and the body, the conductive head being configured to contact the patient for sensing electrical activity and being permeable to allow conductive fluid to be absorbed therethrough; and
   an absorbent material disposed in the inner space for absorbing fluid applied on the head, the absorbent material being in contact with the conductive head and the elongated body.

28. The electrode sensor assembly of claim 27 wherein the elongated body is permeable to allow fluid to be absorbed therethrough, the first end of the elongated conductive body is adapted to receive and absorb fluid thereon.

29. The electrode sensor assembly of claim 28 wherein the elongated body is made of conductive mesh.

30. The electrode sensor assembly of claim 27 wherein the first end is arched.

31. The electrode sensor assembly of claim 27 wherein the elongated conductive body is tubular and the conductive wire is connected to the second end.

32. The electrode sensor assembly of claim 27 wherein the conductive head is connected to the first end of the elongated conductive body with conductive epoxy resin.

33. The electrode sensor assembly of claim 27 wherein the elongated conductive body is a metallic spring, the spring having a predetermined tension so that the spring compresses when pressure is applied on the head, facilitating absorption of conductive fluid by the absorbent material when fluid is disposed on the head and the head is in contact with the patient.

34. The electrode sensor assembly of claim 27 wherein the absorbent material is a sponge material.

35. The electrode sensor assembly of claim 27 wherein the conductive head is made of conductive mesh.

36. The electrode sensor assembly of claim 27 wherein the conductive head is arcuately connected to the first end of the elongated conductive body to define a arcuate surface of the conductive head, the arcuate surface configured to nestle upon contour surfaces of the patient.

37. The electrode sensor assembly of claim 27 further comprising a base having an aperture in which the second end of the elongated body is disposed, the conductive wire being disposed through the aperture.

38. The electrode sensor assembly of claim 27 wherein the elongated conductive body comprises a metallic spring greater than about 2 millimeters in length.

39. An electrode sensor for sensing electrical activity of a patient and allowing a fluid to be permeated therethrough, the electrode sensor comprising:
   a conductive body having first and second ends, the first end being adapted to receive the fluid thereon and to contact the patient for sensing electrical activity of the patient, the conductive body being a permeable metallic spring to allow the fluid to pass therethrough;
   a substrate to which the second end is attached, allowing the elongated conductive body to extend from the substrate to contact the patient;
   a conductive head connected to the first end of the conductive body so that the head is in conductive communication with the body, the connection of the conductive head to the body defining an inner space within the head and the body, the inner space complementing the shapes of the head and the body, the conductive head being configured to contact the patient for sensing electrical activity and being permeable to allow conductive fluid to be absorbed therethrough; and
   an absorbent material disposed in the inner space for absorbing fluid applied on the head, the absorbent material being in contact with the conductive head and the body.

40. The electrode sensor of claim 39 wherein the conductive body is made of conductive mesh.

41. The electrode sensor of claim 39 wherein the conductive body is tubular and a conductive wire is connected to the second end.

42. The electrode sensor of claim 39 wherein the conductive head is connected to the first end of the conductive body with conductive epoxy resin.

43. The electrode sensor of claim 39 wherein the spring has a predetermined tension so that the spring compresses when pressure is applied on the head, facilitating absorption of conductive fluid by the absorbent material when fluid is disposed on the head and the head is in contact with the patient.

44. The electrode sensor of claim 39 wherein the absorbent material is a sponge material.

45. The electrode sensor of claim 39 wherein the conductive head is made of conductive mesh.

46. The electrode sensor of claim 39 wherein the conductive head is arcuately connected to the first end of the conductive body to define a arcuate surface of the conductive head, the arcuate surface configured to nestle upon contour surfaces of the patient.

47. An electrode sensor for sensing electrical activity of a patient and sending signals to a processor, the electrode sensor comprising:
  a conductive head to contact the patient for sensing electrical activity, the conductive head being permeable to allow fluid to be absorbed therethrough;
  an elongated tubular body being greater than 2 millimeters and being permeable to allow fluid be absorbed therethrough, the elongated body having first and second ends and being made of conductive material, the first end being connected to the head so that the elongated body is in conductive communication with the head, the connection of the elongated tubular body to the conductive head defining an inner space within the body and the head, the elongated body having a conductive wire connected to the second end;
  an absorbent material disposed in the inner space for absorbing fluid applied on the head; and
  a ceramic base having an aperture in which the second end of the elongated body is disposed, the conductive wire disposed through the aperture and adapted to be conductively connected to the processor.

48. A method of making an electrode sensor that is attachable to a substrate and usable for sensing electrical activity from a patient, the method comprising:
  providing a conductive head to contact the patient for sensing electrical activity, the conductive head being permeable to allow fluid to pass therethrough;
  providing an elongated tubular body being greater than 2 millimeters in length and having first and second ends and being made of conductive material, the conductive head being permeable to allow fluid to pass therethrough, the elongated body having a conductive wire connected to the second end;
  providing an absorbent material and a ceramic base having an aperture;
  connecting the first end of the elongated tubular body to the conductive head so that the elongated body is in conductive communication with the head, the connection of the elongated tubular body to the conductive head defining an inner space within the body and the head;
  disposing the absorbent material in the inner space for absorbing fluid applied on the head;
  disposing the second end of the elongated body in the aperture, the conductive wire being disposed through the aperture and adapted to be conductively attachable.

49. A method of sensing electrical activity of a patient with an electrode sensor, the method comprising:
  providing a conductive head to contact the patient for sensing electrical activity, the conductive head being permeable to allow conductive fluid to pass therethrough;
  providing an elongated tubular body being greater than 2 millimeters in length and being permeable to allow fluid to pass therethrough, the elongated body having first and second ends and being made of conductive material, the first end being connected to the head so that the elongated body is in conductive communication with the head, the connection of the elongated tubular body to the conductive head defining an inner space within the body and the head, the elongated body having a conductive wire connected to the second end;
  providing an absorbent material disposed in the inner space for absorbing fluid applied on the head; and
  providing a ceramic base having an aperture in which the second end of the elongated body is disposed, the conductive wire disposed through the aperture and adapted to be conductively connected to a processor;
  applying conductive fluid onto the conductive head;
  contacting the conductive head to the patient; and
  maintaining contact of the conductive head to the patient to sense electrical activity of the patient.

50. An electrode sensor assembly comprising:
  a glove; and
  an elongated conductive body having first and second ends and a conductive wire, the first end being adapted to contact the patient for sensing electrical activity of the patient, the elongated conductive body comprising a metallic spring greater than about 2 millimeters in length, and the second end being attached to the glove, allowing the elongated conductive body to extend from the glove to contact the patient.

51. An electrode sensor assembly for sensing electrical activity of a patient, the electrode sensor assembly comprising:
  an elongated conductive body having first and second ends and a conductive wire, the first end being adapted to contact the patient for sensing electrical activity of the patient, the elongated conductive body comprising a metallic spring greater than about 2 millimeters in length; and
  a glove probe to which the second end is attached, allowing the elongated conductive body to extend from the glove probe to contact the patient.

52. The electrode sensor assembly of claim 51 wherein the glove probe is made of an essentially non-conductive, insulative material.

53. An electrode sensor attachable to a substrate for sensing electrical activity of a patient, the electrode sensor comprising:
  an elongated conductive resilient body having first and second ends and a conductive wire, the first end contactable with the patient for sensing electrical activity of the patient, the second end being securable to the substrate;
  a conductive head in conductive communication with the elongated body, the conductive head and the elongated body defining an inner space within the head and the body, the conductive head being configured to contact the patient for sensing electrical activity and being permeable to allow conductive fluid to be absorbed therethrough; and
  an absorbent material within the inner space for absorbing fluid applied on the head, the absorbent material being in contact with the conductive head and the elongated body.

* * * * *